United States Patent [19]

Chen et al.

[11] Patent Number: 5,446,232
[45] Date of Patent: Aug. 29, 1995

[54] REMOVING OXYGEN FROM HYDROCARBON GASES

[75] Inventors: Hang-Chang B. Chen, Getzville; Deborah J. Olsen, Grand Island, both of N.Y.

[73] Assignee: Occidental Chemical Corporation, Niagara Falls, N.Y.

[21] Appl. No.: 195,310

[22] Filed: Feb. 14, 1994

[51] Int. Cl.⁶ .................. C07C 7/148; C07C 7/152; C01B 13/00
[52] U.S. Cl. .................. 585/845; 585/848; 585/849; 585/850; 585/855; 423/219
[58] Field of Search .............. 585/848, 850, 855, 845, 585/849; 423/219

[56] References Cited

U.S. PATENT DOCUMENTS

| | | | |
|---|---|---|---|
| 2,351,167 | 6/1944 | Ware | 266/677 |
| 4,034,062 | 7/1977 | Krueger | 423/219 |
| 4,299,800 | 11/1981 | Nishikawa et al. | 423/219 |
| 5,157,204 | 10/1992 | Brown et al. | 585/850 |

FOREIGN PATENT DOCUMENTS

| | | |
|---|---|---|
| 2553567 | 6/1977 | Germany. |
| 92/10447 | 6/1992 | WIPO. |

*Primary Examiner*—Anthony McFarlane
*Assistant Examiner*—Nhat D. Phan
*Attorney, Agent, or Firm*—Wayne A. Jones; Richard D. Fuerle

[57] ABSTRACT

Disclosed is a method and apparatus for removing oxygen from hydrogen, hydrocarbon, or halogenated hydrocarbon gas which contains about 0.01 to about 10 mole % oxygen. The oxygen removal is accomplished by contacting the gas with a Hopcalite catalyst at a temperature of about 100° to about 300° C. The invention can be part of a process for making 1,2-dichloroethane where, in a first reaction, ethane and chlorine are reacted to make ethylene and hydrogen chloride and, in a second reaction, the ethylene and hydrogen chloride are reacted with excess oxygen to make the 1,2-dichloroethane. The unreacted ethane can be recycled to the first step after the method of the invention is applied to remove the oxygen.

30 Claims, 1 Drawing Sheet

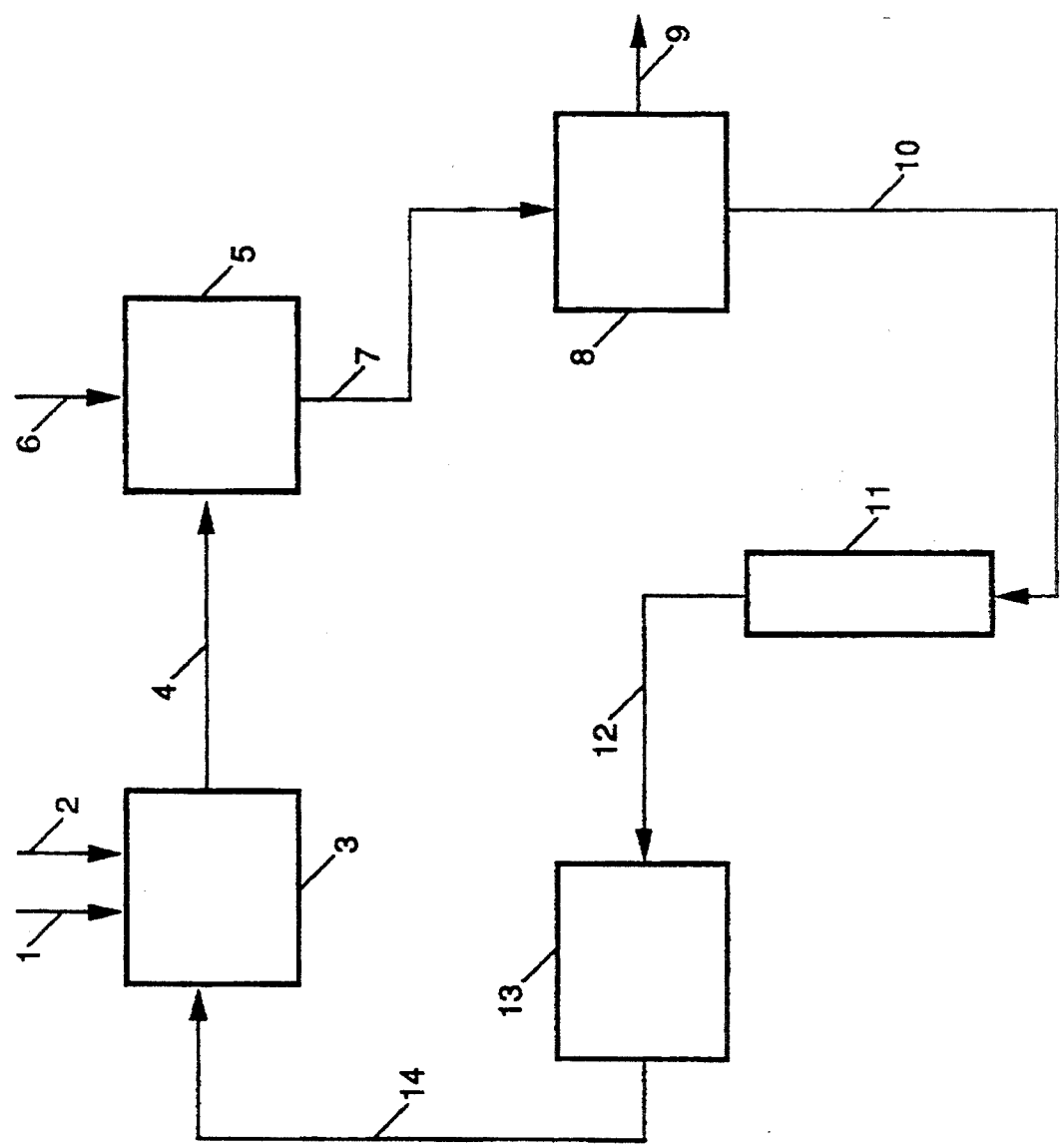

REMOVING OXYGEN FROM HYDROCARBON GASES

BACKGROUND OF THE INVENTION

This invention relates to a method of removing oxygen from hydrogen, hydrocarbon gases, and halogenated hydrocarbon gases that contain about 0.01 to about 10 mole % oxygen. In particular, it relates to the use of a Hopcalite catalyst at a temperature of about 100° to about 300° C. to remove oxygen from these gases.

A new process for producing 1,2-dichloroethane (EDC) in two steps is disclosed in WO 92/10447, herein incorporated by reference. In that process, ethane and chlorine are first reacted (in a two step reaction) to form ethylene and hydrogen chloride. That reaction occurs at high temperatures and the presence of oxygen in the reaction can burn the hydrocarbons and result in an explosion hazard. Also, the burning of the hydrocarbons with oxygen results in the formation of water which, in the presence of the hydrogen chloride, produces corrosive hydrochloric acid. Thus, it is necessary to exclude oxygen during that reaction.

The product of the reaction, ethylene and hydrogen chloride, is reacted with oxygen in an oxychlorinator at a lower temperature to form EDC. Excess oxygen is used in the oxychlorinator and the EDC product contains not only excess oxygen but also unreacted ethane from the first reaction. Once the EDC has been removed, the remaining mixture, which is mostly ethane, could be recycled to the first reaction, provided that the oxygen can be removed from it first. (Until the discovery of this new process, oxygen removal was not necessary because conventional processes for producing EDC began with ethylene, not ethane.)

Hopcalite catalysts, a mixture of copper and manganese oxides, are widely used to remove pollutants from air by catalyzing the reaction of the pollutants with oxygen. For example, Hopcalite catalysts have been used to catalyze the reaction of carbon monoxide, nitrogen oxides, ozone, and chlorinated hydrocarbons. In these reactions, the pollutant is present at a very low concentration in a huge excess of oxygen. The catalyst is thereby maintained in a higher oxidation state (CuO and $MnO_2$) by reaction with oxygen and immediately returns to the higher oxidation state after being reduced by reaction with a pollutant.

SUMMARY OF THE INVENTION

We have discovered that Hopcalite and related catalysts can be used in a lower oxidation state to remove very small amounts of oxygen from large excesses of hydrogen, hydrocarbons, or halogenated hydrocarbons. The removal occurs by the reaction of the oxygen with the hydrogen or hydrocarbon to produce carbon dioxide and water (or just water if hydrogen is the only reactant). Because of this invention, a mixture of unreacted ethane and oxygen from the oxychlorination can now be treated to remove the oxygen so that the remaining ethane can be recycled and reacted with chlorine to produce more ethylene.

BRIEF DESCRIPTION OF THE DRAWINGS

The accompanying drawing is a diagramatic view of a certain presently preferred embodiment of an apparatus for producing EDC from ethane and hydrochloric acid according to this invention.

DESCRIPTION OF THE PREFERRED EMBODIMENT

In the drawing, ethane in line 1 and chlorine in line 2 are reacted in adiabatic reactor 3 at a temperature of about 600° to about 700° C. to form ethylene and hydrogen chloride according to the reaction

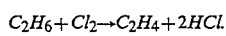

$$C_2H_6 + Cl_2 \rightarrow C_2H_4 + 2HCl.$$

The ethylene and hydrogen chloride product are sent through line 4 to oxychlorinator 5 where oxygen is added through line 6 to produce EDC according to the reaction

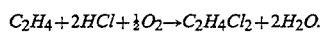

$$C_2H_4 + 2HCl + \tfrac{1}{2}O_2 \rightarrow C_2H_4Cl_2 + 2H_2O.$$

This reaction typically occurs at a temperature of about 200° to about 300° C. The product is sent through line 7 to gas-liquid separator 8 where the liquid EDC and water products are removed from the gas mixture through line 9. (The EDC can be separated from the water by phase separation followed by distillation in a drying column, not shown.) The remaining gas mixture is sent through line 10 to oxygen scavenger 11, which contains heated Hopcalite or related catalyst. The composition of the gases in line 10 of the drawing is typically about 40 to about 90 mole % ethane, about 5 to about 40 mole % ethylene, about 0 to about 10 mole % ethyl chloride, about 0 to about 5 mole % methane, and about 0.01 to about 2 mole % oxygen. Oxygen scavenger 11 is preferably a column packed with Hopcalite catalyst heated to about 200° to about 225° C. The gas mixture passes up through the column resulting in the reaction of oxygen with the hydrocarbons present to form water and carbon dioxide. The mixture then passes through line 12 to water absorber 13. Water removal can be accomplished, for example, by means of a molecular sieve or alumina. The moisture-free mixture, primarily ethane, then passes through line 14 back to adiabatic reactor 3.

Carbon dioxide removal from the recycled gases is optional, as carbon dioxide is inert in the reactions. However, its concentration will gradually increase until it affects the efficiency of the process. Carbon dioxide can be removed by using a caustic wash or a compressor and distillation column prior to removal of the water from the recycled gases, or by periodic purging.

The method and apparatus of this invention are applicable to hydrogen and to any hydrocarbon or halogenated hydrocarbon gas having 1 to 4 carbon atoms. Examples include ethane, ethylene, methane, propane, isopropane, butane, ethyl chloride, butadiene, propyl chloride and acetylene, as well as mixtures of these gases. The gases contain small amounts of oxygen, typically about 0.01 to about 10 mole % and preferably about 0.1 to about 2 mole %.

The catalysts useful in this invention are oxides of manganese, vanadium, tungsten, iron, molybdenum, and chromium and oxides and chlorides of copper, nickel, cobalt, and silver. In particular, the catalysts are $Mn_2O_3$, $MnO_2$, $V_2O_5$, $WO_3$, $Fe_2O_3$, $MoO_3$, $Cr_2O_3$, CuO, $CuCl_2$, NiO, $NiCl_2$, $Co_3O_4$, $CoCl_3$, $Ag_2O$, and AgCl. Mixtures of these catalysts can also be used. The preferred catalysts are $MnO_2$ and CuO. Since $MnO_2$ is believed to be active against hydrocarbons (e.g., $CH_4$, $C_2H_4$, and $C_2H_6$) and CuO is believed to be active against hydrogen and ethyl chloride, a mixture of $MnO_2$ and CuO is preferred for many industrial applications. The mixture can be about 1 to about 99 wt % $Mn_2O_3$ or $MnO_2$ to about 1 to about 99 wt % CuO, but about 70 to about 95 wt % $Mn_2O_3$ or $MnO_2$ and about 5 to about 30 wt % CuO is preferred. The most preferred mixture of $Mn_2O_3$ or $MnO_2$ and CuO is known as a "Hopcalite catalyst" and is about 86 wt % $MnO_2$ and 14 wt % CuO.

Because the hydrocarbon gas is present in much greater quantities than oxygen, most of the catalyst will be present in its lower oxidation state, e.g., $Cu_2O$, $Mn_2O_3$, and MnO. In the catalytic reaction of the oxygen with the hydrocarbon the catalyst is oxidized to its higher oxidation state, CuO and $MnO_2$, but then is immediately reduced by the large excess of hydrocarbons.

The amount of catalyst used should be sufficient to give a gas hourly space velocity (GHSV) of about 100 to about 4000 $hr^{-1}$. (The space velocity is the volume of gas that passes over the catalyst per unit time divided by the volume of catalyst used). Lower space velocities can be used, but they require impractical large amounts of catalyst; at higher space velocities the efficiency of the catalyst may decrease unless higher temperatures are used.

The temperature of the catalytic reaction can be about 100° to about 300° C. and is preferably about 200° to about 250° C., but will depend upon the particular hydrocarbon or mix of hydrocarbons being treated. Temperatures of less than 100° C. should not be used because that can result in water being trapped on the catalyst which may reduce its activity.

The following examples further illustrate this invention.

EXAMPLES

EXAMPLE 1

Two types of Hopcalite catalyst, acquired from Callery Chemical Company, were evaluated. Both catalysts had a grain size of 6 to 14 mesh. The apparent densities of Type 26599 and Type 21215 Hopcalite are $\geq 0.95$ and $\geq 0.75$ g/cm, respectively. Type 26599 has a nominal moisture content of $\leq 0.5\%$, while Type 21215 can tolerate adsorption of up to 4 wt % of water before catalyst activity is significantly reduced.

The fixed bed reactor was packed with a preselected amount of catalyst in a $\frac{3}{4}''$ α-SiC tube. Reactor temperature was maintained by a temperature-controlled tube furnace. For each test, cylinder nitrogen purged the entire system while the reactor was heated to the desired temperature. Once the temperature was reached, nitrogen was replaced by the reaction feed gases. The reactant flow rates were manually controlled by metering valves and monitored by digital mass flow meters and rotameters. The feed gases were fed into a premixer to ensure proper mixing. The gas mixture then passed through the preheated reactor tube.

Once the reaction reached steady state at each set of conditions, gas chromatography (GC) samples of feed and product streams were taken periodically. A GC method was developed to provide high sensitivity for oxygen, carbon monoxide, and carbon dioxide detections.

In all cases 12 ml of catalyst was used and the reactor pressure was 0 psig. Ethane, ethylene, methane, and oxygen in volumetric flow rates of 130, 15, 4, 0.73 ml/min respectively, constituted 1 unit of gas mixture. The following tables give the results.

TABLE 1

Hopcalite 26599, GHSV = 748.65 $hr^{-1}$, no hydrogen, 1 unit/minute of gas mixture.

| Reactor Temp/°C. | 25 | 198 | 224 | 248 | 276 |
|---|---|---|---|---|---|
| $O_2$, removed (%) | 0.00 | 90.97 | 98.66 | 96.70 | 96.41 |

TABLE 2

Hopcalite 26599, GHSV = 1497.25 $hr^{-1}$, no hydrogen, 2 units/min of gas mixture.

| Reactor Temp/°C. | 25 | 193 | 219 | 246 | 278 |
|---|---|---|---|---|---|
| $O_2$ Removed (%) | 0.00 | 52.13 | 91.76 | 98.23 | 98.26 |

TABLE 3

Hopcalite 26599, GHSV = 2246 $hr^{-1}$, no hydrogen, 3 units of gas mixture.

| Reactor Temp/°C. | 25 | 198 | 221 | 250 | 279 |
|---|---|---|---|---|---|
| $O_2$ Removed (%) | 0.0 | 52.60 | 90.67 | 96.82 | 97.82 |

TABLE 4

Hopcalite 26599, GHSV = about 1500 $hr^{-1}$, 2 units of gas mixture plus hydrogen

| Hydrogen (ml/min) | 0 | 2.9 | 2.9 | 2.9 | 2.9 |
|---|---|---|---|---|---|
| Reactor Temp/°C. | 25 | 199 | 225 | 251 | 274 |
| $O_2$ Removed (%) | 0.00 | 79.94 | 95.91 | 99.54 | 99.29 |

TABLE 5

Hopcalite 26599, GHSV = 1557.25 $hr^{-1}$, 2 units of gas mixture plus 12 ml/min ethyl chloride

| Reactor Temp/°C. | 25 | 195 | 226 | 248 | 276 |
|---|---|---|---|---|---|
| $O_2$ Removed (%) | 0.00 | 96.70 | 98.88 | 98.91 | 98.14 |

TABLE 6

Hopcalite 21215, GHSV = 1527.25 $hr^{-1}$, 2 units of gas mixture plus 6 ml/min ethyl chloride

| Reactor Temp (°C.) | 25 | 125 | 133 | 149 | 154 | 174 | 178 |
|---|---|---|---|---|---|---|---|
| $O_2$, Removed (%) | 0.00 | 61.90 | 73.15 | 97.32 | 89.52 | 99.33 | 98.68 |

The data clearly show that Type 26599 Hopcalite consistently reduces the oxygen concentration from as high as 0.87% down to about 50 ppm. The data also shows that a reactor temperature of about 225° to 250° C. is most effective and that the space velocity can be varied from 750 to 2250 $hr^{-1}$. By comparing Tables 2 and 4 it is obvious that the process requires no hydrogen to facilitate the oxygen removal. As shown in Table 5, adding about 4% ethyl chloride in the simulated recycle mixture did not have an adverse effect on Type 26599 Hopcalite effectiveness.

As shown in Table 6, when the recycle stream contained about 3% ethyl chloride essentially all the oxygen in the stream was removed by maintaining the catalytic reactor at 175° C.

Another approach investigated was to minimize the thermal dehydrochlorination of ethyl chloride by decreasing the reactor temperature. With no ethyl chloride and hydrogen in the simulated feed, Type 21215 Hopcalite removed >99% of the oxygen at a temperature of 125° to 150° C. and a space velocity of 1500 hr$^{-1}$.

EXAMPLE 2

Sustained bench-scale evaluation was performed to examine the service life and oxygen removal efficiency of Type 21215 Hopcalite catalyst. The molar concentrations of ethane, ethylene, ethyl chloride, methane, and oxygen in the simulated recycle stream were 81.7%, 13.3%, 2.8%, 1.5%, and 0.7%, respectively. The gas hourly space velocity was set at 1500 hr$^{-1}$. For the first 160 hours of operation, nearly 100% oxygen removal was consistently achieved at a reactor temperature of 175° C. The catalyst activity appeared to remain constant. Ethyl chloride in the feed showed no adverse effect on the catalyst performance. In a single fixed bed reactor, the majority of the oxygen feed was converted by reacting with ethylene, and the residual oxygen was eliminated by reacting with methane.

Hopcalite catalyst effectiveness declined slightly but steadily as the sustained operation exceeded 175 hours. The decline was believed to be due to the product water absorbed on the catalyst. It was found that by adjusting the reactor temperature to 200° C., the catalyst would self-regenerate and maintain high activity.

The study was concluded as the total operation time reached 400 hours. Even with constant operation and temperature cycling, the system consistently achieved nearly 100% oxygen removal.

We claim:

1. A method of removing oxygen from a gas selected from the group consisting of hydrogen, hydrocarbons from $C_1$ to $C_4$, halogenated hydrocarbons from $C_1$ to $C_4$, and mixtures thereof, where said gas contains about 0.01 to about 10 mole % oxygen, comprising contacting said gas at a reaction temperature of about 100° to about 300° C. with a catalyst selected from the group consisting of $Mn_2O_3$, $MnO_2$, $V_2O_5$, $WO_3$, $MoO_3$, $Cr_2O_3$, $CuCl_2$, $NiO$, $NiCl_2$, $CoCl_3$, mixtures thereof, and mixtures thereof with $Fe_2O_3$, $CuO$, $Co_3O_4$, $Ag_2O$, or $AgCl$.

2. A method according to claim 1 wherein the concentration of oxygen in said gas is about 0.1 to about 2 mole %.

3. A method according to claim 1 wherein said gas comprises ethane.

4. A method according to claim 1 wherein said gas moves over said catalyst at a space velocity of about 100 to about 4000 hr$^{-1}$.

5. A method according to claim 1 wherein said gas contacts said catalyst at a reaction temperature of about 200° to about 250° C.

6. A method according to claim 1 wherein said catalyst is a Hopcalite catalyst.

7. A method according to claim 1 wherein said catalyst is $Mn_2O_3$.

8. A method according to claim 1 wherein said catalyst is $MnO_2$.

9. A method according to claim 1 wherein said catalyst is $V_2O_5$.

10. A method according to claim 1 wherein said catalyst is $WO_3$.

11. A method according to claim 1 wherein said catalyst is $MoO_3$.

12. A method according to claim 1 wherein said catalyst is $Cr_2O_3$.

13. A method according to claim 1 wherein said catalyst is $CuCl_2$.

14. A method according to claim 1 wherein said catalyst is $NiO$.

15. A method according to claim 1 wherein said catalyst is $NiCl_2$.

16. A method according to claim 1 wherein said catalyst is $CoCl_3$.

17. A method of removing oxygen from a gas selected from the group consisting of hydrogen, hydrocarbons from $C_1$ to $C_4$, chlorinated hydrocarbons from $C_1$ to $C_4$, and mixtures thereof, where said gas contains about 0.01 to about 10 mole % oxygen, comprising passing said gas at a reaction temperature of about 100° to about 300° C. through a catalyst which comprises a mixture of about 1 to about 99 wt % $Mn_2O_3$ or $MnO_2$ and about 1 to about 99 wt % $CuO$.

18. A method according to claim 17 wherein said gas comprises ethane.

19. A method according to claim 17 wherein said catalyst comprises about 70 to about 95 wt % $Mn_2O_3$ or $MnO_2$ and about 5 to about 30 wt % $CuO$.

20. A method according to claim 17 wherein said catalyst is a Hopcalite catalyst.

21. A method according to claim 20 wherein said gas is about 40 to about 90 mole % ethane, about 5 to about 40 mole % ethylene, up to about 10 mole % ethyl chloride, up to about 5 mole % methane, and about 0.8 to about 1 mole % oxygen.

22. A method according to claim 20 wherein said gas contacts said catalyst at a reaction temperature of about 200° to about 250° C.

23. A method according to claim 20 wherein water is formed in said reaction and is removed using a molecular sieve.

24. A method according to claim 20 wherein water is formed in said reaction and is removed using alumina.

25. A method according to claim 20 wherein said gas moves over said catalyst at a space velocity of about 100 to about 4000 hours$^-$.

26. A method according to claim 20 wherein carbon dioxide is periodically removed from said mixture by purging.

27. A method of removing oxygen from a gas which comprises a mixture of about 40 to about 90 mole % ethane, about 5 to about 40 mole % ethylene, about 0 to about 10 mole % ethyl chloride, about 0 to about 5 mole % methane, and about 0.01 to about 2 mole % oxygen comprising passing said gas at a reaction temperature of about 100° to about 300° C. through a Hopcalite catalyst.

28. A method according to claim 27 wherein said gas is produced by reacting ethane with chlorine at about 600° to about 700° C. to make a product which comprises ethylene and hydrogen chloride, reacting said product with excess oxygen at about 200° to about 300° C. to produce a mixture which comprises 1,2-dichloroethane and contains unreacted ethane and oxygen, and separating said 1,2-dichloroethane from said mixture.

29. A method according to claim 27 wherein said Hopcalite catalyst is heated to about 200° to about 225° C.

30. A method according to claim 27 wherein the concentration of oxygen in said gas is about 0.1 to about 2 mole %.

* * * * *